(12) United States Patent  
Markham

(10) Patent No.: US 9,155,758 B2
(45) Date of Patent: *Oct. 13, 2015

(54) TREATMENT OF CHRONIC PROGRESSIVE HEART FAILURE

(75) Inventor: Bruce Edward Markham, Novi, MI (US)

(73) Assignee: PHRIXUS PHARMACEUTICALS, INC., Ann Arbor, MI (US)

( * ) Notice: Subject to any disclaimer, the term of this patent is extended or adjusted under 35 U.S.C. 154(b) by 416 days.

This patent is subject to a terminal disclaimer.

(21) Appl. No.: 12/309,803

(22) PCT Filed: Aug. 1, 2007

(86) PCT No.: PCT/US2007/017182

§ 371 (c)(1),
(2), (4) Date: May 7, 2009

(87) PCT Pub. No.: WO2008/016640

PCT Pub. Date: Feb. 7, 2008

(65) Prior Publication Data

US 2009/0246162 A1   Oct. 1, 2009

Related U.S. Application Data

(60) Provisional application No. 60/834,728, filed on Aug. 1, 2006.

(51) Int. Cl.
*A61K 31/77* (2006.01)
*A61K 31/765* (2006.01)

(52) U.S. Cl.
CPC ............... *A61K 31/77* (2013.01); *A61K 31/765* (2013.01)

(58) Field of Classification Search
CPC .......................... A61K 31/77; A61K 31/765
See application file for complete search history.

(56) References Cited

U.S. PATENT DOCUMENTS

| | | | |
|---|---|---|---|
| 5,198,211 | A | 3/1993 | Hunter et al. |
| 5,605,687 | A | 2/1997 | Lee |
| 5,733,572 | A | 3/1998 | Unger et al. |
| 6,342,247 | B1 | 1/2002 | Ku et al. |
| 6,747,064 | B2 | 6/2004 | Emanuele et al. |
| 6,761,824 | B2 | 7/2004 | Reeve et al. |
| 6,977,045 | B2 | 12/2005 | Reeve et al. |

(Continued)

FOREIGN PATENT DOCUMENTS

| | | |
|---|---|---|
| WO | WO 92/22202 | 12/1992 |
| WO | WO 00/21543 | 4/2000 |

(Continued)

OTHER PUBLICATIONS

Alexander Justicz, et al, Reduction of Myocardial Infarct Size by Poloxamer 188 and Mannitol in a Canine Model, 122 Am. Heart J 671 (Sep. 1991) (Abstract).*

(Continued)

*Primary Examiner* — Ernst V Arnold
*Assistant Examiner* — Kyung Sook Chang
(74) *Attorney, Agent, or Firm* — Honigman Miller Schwartz and Cohn LLP; Fernando Alberdi; Jonathan P. O'Brien

(57) ABSTRACT

The invention provides a method for treating or preventing heart failure in a subject, which includes administering to the subject in need thereof a therapeutically effective amount of a Poloxamer (e.g., Poloxamer 188).

4 Claims, 4 Drawing Sheets

LV End Diastolic Pressure in Moderate to Severe Heart Failure Treated with 4.6 mg/kg P188

LVEDP (mmHg) in Sham, heart failure animals untreated (CHF + No Rx), heart failure treated with 4.6 mg/kg P188 (CHF + 4.6) and Sham treated with 4.6 mg/kg.
* $P < 0.05$ vs CHF No rx and CHF 4.6;  ** $P < 0.05$ vs CHF No Rx and Sham ± 4.6 mg/kg.
Data are mean ± SE, N = 4 for sham, 6 for CHF, 11 for (4.6 sham and CHF).

(56) References Cited

U.S. PATENT DOCUMENTS

| | | | |
|---|---|---|---|
| 7,846,426 | B2 | 12/2010 | Metzger et al. |
| 8,372,387 | B2 | 2/2013 | Markham |
| 8,580,245 | B2 | 11/2013 | Metzger et al. |
| 2003/0124190 | A1 | 7/2003 | Williams et al. |
| 2004/0053277 | A1 | 3/2004 | Zhang et al. |
| 2004/0265388 | A1 | 12/2004 | Zhang et al. |
| 2006/0121016 | A1 | 6/2006 | Lee |
| 2007/0237740 | A1 | 10/2007 | Reddington et al. |
| 2008/0260681 | A1* | 10/2008 | Metzger et al. ............ 424/78.38 |
| 2010/0178269 | A1* | 7/2010 | Markham .................. 424/78.18 |
| 2011/0033412 | A1 | 2/2011 | Ng et al. |

FOREIGN PATENT DOCUMENTS

| | | |
|---|---|---|
| WO | WO 02/065834 | 8/2002 |
| WO | WO 2006/037031 | 4/2006 |
| WO | WO 2006/091941 | 8/2006 |
| WO | WO2006/100017 | 9/2006 |
| WO | WO2007/088123 | 8/2007 |
| WO | WO 2008/016640 | 2/2008 |
| WO | WO 2008/124088 | 10/2008 |
| WO | WO 2009/078978 | 6/2009 |
| WO | WO 2009/079562 | 6/2009 |
| WO | WO2011/066201 | 6/2011 |

OTHER PUBLICATIONS

F. Abroug, et al, Cardiac Dysfunction and Pulmonary Edema Following Scorpion Envenomation, 100 Chest 1057 (1991).*

Alexander Justicz, et al, Reduction of Myocardial Infarct Size by Poloxamer 188 and Mannitol in a Canine Model, 122 Am. Heart J 671 (Sep. 1991).*

WebMd, "Heart Failure Medication Option" (webmd.com, last visit Dec. 12, 2012).*

Spurney et al. "Membrane sealant poloxamer P188 protects against isoproterenol induced cardiomyopathy in dystrophin deficient mice", BMC Cardiovascular Disorders (2011).*

Ventricular systolic dysfunction—Heart failure symptoms: [retrieved on Jul. 10, 2014 from on-line website; http://cvphysiology.com/Heart%20Failure/HF005.htm] (published in 2007).*

Chatterjee et al, "Systolic and diastolic Heart Failure: Differences and Similarities", Journal of Cardiac Failure, pp. 569-576 vol. 13 No. 7, 2007.*

Adams-Graves, Patricia, et al., "RheothRx (Poloxamer 118) Injection for the Acute Painful Episode of Sickle Cell Disease: A Pilot Study", Blood, 1997, vol. 90, No. 5, pp. 2041-2046.

Angeja, Brad G., et al., "Evaluation and Management of Diastolic Heart Failure" Circulation, 2003, vol. 107, pp. 659-663.

Baczko, Istvan, et al., "Pharmacological activation of plasma-membrane KATP channels reduces reoxygenation-induced Ca2+ overload in cardiac myocytes via modulation of the diastolic membrane potential", British Journal of Pharmacology, Mar. 2004, vol. 141, No. 6, pp. 1059-1067.

Balghith, Mohammed, et al., "Assessment of diastolic dysfunction after acute myocardial infarction using Doppler echocardiography", Canadian Journal Cardiology, Jan. 2002, vol. 18, No. 1, pp. 69-77.

Blake, Derek J., et al., "Function and Genetics of Dystrophin and Dystrophin-Related Proteins in Muscle", Physiol Rev, Apr. 2002, vol. 82, pp. 291-329.

Borgens, Richard B., et al., "Subcutaneous Tri-Block Copolymer Produces Recovery From Spinal Cord Injury", Journal of Neuroscience Research, 2004, vol. 76, pp. 141-154.

Bulfield, Grahame, et al., "X chromosome-linked muscular dystrophy (mdx) in the mouse", Proc. Natl. Acad. Sci. USA, 1984, vol. 81, pp. 1189-1192.

Chareonthaitawee, P., et al., "The impact of time to thrombolytic treatment on outcome in patients with acute myocardial infarction", Heart, 2000, vol. 84, pp. 142-148.

Emanuele, R. Martin, et al., "FLOCOR: a new anti-adhesive, rheologic agent.", Expert Opin Investig Drugs, 1998, vol. 7, No. 7, pp. 1193-1200.

Finstere, Josef, et al., "The Heart in Human Dystophinopathies", Cardiology, vol. 99, No. 1, pp. 1-19.

Gibbs, Winter J., et al., "Purified Poloxamer 188 for Sickle Cell Vaso-Occlusive Crisis", The Annals of Pharmacotherapy, Feb. 2004, vol. 38, No. 2, pp. 320-324.

Goyenvalle, Aurélie, et al., "Rescue of Dystrophic Muscle Through U7 snRNA-mediated Exon Skipping", Science, 2004, vol. 306, pp. 1796-1799.

Gregorevic, Paul, et al., "Systemic delivery of genes to strained muscles using adeno-associated viral vectors", Nature Medicine, Aug. 2004, vol. 10, No. 8, pp. 828-834.

Grover, Frederick L., et al., "Effect of a Nonionic Surface-Active Agent on Blood Viscosity and Platelet Adhesiveness", Circulation, 1969, vol. 39, I-1249.

Halacheva, Silvia, et al., "Poly(glycidol)-Based Analogues to Pluronic Block Copolymers. Synthesis and Aqueous Solution Properties", Macromolecules, 2006, vol. 39, pp. 6845-6852.

Head, Stewart I., et al., "Abnormalities in structure and function of limb skeletal muscle fibers or dystrophy mdx mice", Proceedings: Biological Sciences, May 22, 1992, vol. 248, No. 1322, pp. 163-169.

Hoffman, Eric P., et al., "Dystrophin: The Protein Product of the Duchenne Muscular Dystrophy Locus", Cell, 1987, vol. 51, pp. 919-928.

Hunt, Sharon A., et al., "ACC/AHA Guidelines for the Evaluation and Management of Chronic Heart Failure in the Adult: Executive Summary A Report of the American College of Cardiology/American Heart Association Task Force on Practice Guidelines (Committee to Revise the 1995 Guidelines for the Evaluation and Management of Heart Failure)", Circulation, 2001, vol. 104, pp. 2996-3007.

Kabanov, Alexander V., et al., "Pluronic block copolymers for overcoming drug resistance in cancer", Advanced Drug Delivery Reviews, 2002, vol. 54, pp. 758-779.

Kainthan, Rajesh Kumar, et al., "Biocompatibility Testing of Branched and Linear Polyglycidol", Biomacromolecules, Mar. 2006, vol. 7, No. 3, pp. 703-709.

Kaprielian, Raffi R., et al., "Dystrophin and the cardiomyocyte membrane cytoskeleton in the healthy and failing heart", Heart Failure Reviews, 2000, vol. 5, pp. 221-238.

Kawada, Tomie, et al., "A novel paradigm for the therapeutic basis of advanced heart failure-assessment by gene therapy", Pharmacology & Therapeutics, 2005, vol. 107, pp. 31-43.

Lamb, G. D., et al., "Raised intracellular [Ca2+] abolishes excitation-contraction coupling in skeletal muscle fibers of rat and toad", Journal of Physiology, 1985, vol. 489, No. 2, pp. 349-362.

Lee, Raphael C., et al., "Pharmaceutical therapies for sealing of premeabilized cell membranes in electrical injuries", Annals New York Academy of Sciences, 1999, vol. 888, pp. 266-273.

Lee, Raphael C., et al., "Surfactant-induced sealing of electropermeabilizied skeletal muscle membranes in vivo", Proc. Natl. Acad. Sci. USA, 1992, vol. 89, pp. 4524-4528.

Li, Sheng, et al., "A highly functional mini-dystrophin/GFP fusion gene for cell and gene therapy studies of Duchenne muscular dystrophy", Human Molecular Genetics, 2006, vol. 15, No. 10, pp. 1610-1622.

Liang, Qiangrong, et al., "Redefining the roles of p38 and JNK signaling in cardiac hypertrophy: dichotomy between cultured myocytes and animal models", Journal of Molecular and Cellular Cardiology, 2003, vol. 35, pp. 1385-1394.

Lynch, Gordon S., et al., "Force and power output of fast and slow skeletal muscles from mdx mice 6-28 months old", Journal of Physiology, 2001, vol. 535, No. 2, pp. 591-600.

Marks, Jeremy D., et al., "Amphiphillic, tri-block copolymers provide potent, membrane-targeted neuroprotection", The FASEB Journal, 2001, vol. 15, pp. 1107-1109.

Maskarinec, Stacey A., et al., "Direct Observation of Poloxamer 188 Insertion into Lipid Monolayers", Biophysical Journal, Mar. 2002, vol. 82, pp. 1453-1459.

Maynard, Charles, et al., "Randomized, controlled trial of RheothRx (poloxamer 188) in patients with suspected acute myocardial infarction", American Heart Journal, May 1, 1998, vol. 135, No. 5, pp. 797-804.

(56) References Cited

OTHER PUBLICATIONS

Merchant, F. A., et al., "Poloxamer 188 Enhances Functional Recovery of Lethally Heat-Shocked Fibroblasts", Journal of Surgical Research, 1998, vol. 74, pp. 131-140.
Michele, Daniel E., et al., "Cardiac Dysfunction in Hypertrophic Cardiomyopathy Mutant Tropomyosin Mice is Transgene-Dependant, Hypertrophy-Independent, and Improved by β-Blockade", Circulation Research, 2002, vol. 91, pp. 255-262.
Modi, Nishit B., "Flocor CytRx Corp", IDrugs, 1999, vol. 2, No. 4, pp. 366-374.
Mutoni, Francesco, "Cardiomyopathy in muscular dystrophies", Current Opinion in Neurology, 2003, vol. 16, pp. 577-583.
Myocardial Preconditioning, Specialty: Myocardial lschemia/Function/Metabolism, Monday Afternoon, Earnest N Morial Convention Center, 286-287, Abstracts 641-650.
Ohlendieck, Kay, et al., "Dystrophin-associated Proteins Are Greatly Reduced in Skeletal Muscle From mdx Mice", Journal of Cell Biology, Dec. 1991, vol. 115, No. 6, pp. 1685-1694.
O'Keefe, James H., Jr., et al., "Poloxamer-188 as an Adjunct to Primary Percutaneous Transluminal Coronary Angioplasty for Acute Myocardial Infarction", American Journal of Cardiology, Oct. 1, 1996, vol. 78, pp. 747-750.
Pasternak, Carmela, et al., "Mechanical Function of Dystrophin in Muscle Cells", The Journal of Cell Biology, Feb. 1995, vol. 128, No. 3, pp. 355-361.
Petrof, Basil J., "Molecular Pathophysiology of Myofiber Injury in Deficiencies of the Dystrophin-Glycoprotein Complex", American Journal of Physical Medicine & Rehabilitation, Nov. 2002, vol. 81, No. 11, pp. S162-S174.
Raev, Dimitar C., "Which Left Ventricular Function Is Impaired Earlier in the Evolution of Diabetic Cardiomyopathy? An echocardiographic study of young type I diabetic patients", Diabetes Care, Jul. 1994, vol. 17, No. 7, pp. 633-639.
Reeve, Loraine E., "The Poloxamers: Their Chemistry and Medical Application", In: Handbook of Biodegradable Polymers, Harwood Academic Pub, 1997, pp. 231-249.
Schaer, Gary L., et al., "Beneficial effects of RheothRx injection in patients receiving thrombolytic therapy for acute myocardial infarction. Results of a randomized, double-blind, placebo-controlled trial", Circulation, Aug. 1996, vol. 94, No. 3, pp. 298-370.
Schmolka, Irving R., "A Review of Block Polymer Surfactants", Journal of the American Oil Chemists' Society, Mar. 1977, vol. 54, pp. 110-116.
Shibata, Marcelo, et al., "Study of the Effects of Nebivolol Intervention on Outcomes and Rehospitalization in Seniors with Heart Failure (SENIORS). Rational and design", International Journal of Cardiology, 2002, vol. 86, pp. 77-85.
Sokabe, Masahiro, et al., "Blockers and Activators for Stretch-Activated Ion Channels of Chick Skeletal Muscle", Annals New York Academy of Science, 1993, vol. 707, pp. 417-420.
Squire, S., et al., "Prevention of pathology in mdx mice by expression of utrophin: analysis using an inducible transgenic expression system", Human Molecular Genetics, 2002. vol. 11, No. 26, pp. 3333-3344.
Steinhardt, Richard A., "Cardiology: rips repaired", Nature. Aug. 18, 2005, vol. 436, No. 7053, p. 925.
Straub, Volker, et al., "Muscular dystrophies and the dystrophin-glycoprotein complex", Current Opinion in Neurology, 1997, vol. 10, pp. 168-175.
Takahashi, Masaya, et al., "Effects of ACE inhibitor and AT1 blocker on dystrophin-related proteins and calpain in failing heart", Cardiovascular Research, 2005, vol. 65, pp. 356-365.
Torrente, Yvan, et al., "Human circulating AC133+ stem cells restore dystrophin expression and ameliorate function in dystrophic skeletal muscle", The Journal of Clinical Investigation, Jul. 2004, vol. 114, No. 2, pp. 182-195.
Toth, K., et al., "The effect of RheothRx Injection on the hemorheological parameters in patients with acute myocardial infraction", Clinical Hemorheology and Microcirculation, 1997, vol. 17, No. 2, pp. 117-125.
Townsend, DeWayne, et al., "Cardiomyopathy of Duchenne muscular dystrophy: pathogenesis and prospect of membrane sealants as a new therapeutic approach", Expert Review of Cardiovascular Therapy, Jan. 2007, vol. 5, No. 1, pp. 99-109.
Vanderbrouck, Clarisse, et al., "Involvement of TRPC in the abnormal calcium influx observed in Dystrophic (mdx) mouse skeletal muscle fibers", Journal of Cell Biology, Sep. 16, 2002, vol. 158, No. 6, pp. 1089-1096.
Verburg, Esther, et al., "Disruption of excitation-contraction coupling and titin by endogenous Ca2+-activated proteases in toad muscle fibers", J Phsiol, 2005, vol. 564, No. 3, pp. 775-789.
Wu, Guohui, et al., "Lipid Corralling and Poloxamer Squeeze-Out in Membranes", Physical Review Letters, 2004, vol. 93, No. 2, 028101. 1-028101.4.
Yasuda, Soichiro, et al., "Dystrophic heart failure blocked by membrane sealant poloxamer", Nature, Nature Publishing Group, London, UK, Aug. 18, 2005, vol. 436, No. 7053, pp. 1025-1029.
Yasuda, So-ichiro, et al., "Membrane Sealant Poloxamer 188 Corrects the Primary Defect Caused by Dystrophin Deficiency in Single Cardiac Myocytes from Mdx Mice", Circulation, Oct. 2004, vol. 110, No. 17, p. 135.
Yeung, Ella W., et al., "Effects of stretched-activated channel blockers on [Ca2+]i and muscle damage in the mdx mouse", J Physiol, 2005, vol. 562, No. 2, pp. 367-380.
Yusuf, S., et al., "Effects of RheothRx on Mortality, Morbidity, Left Ventricular Function, and Infarct Size in Patients With Acute Myocardial Infarction", Collaborative Organization for RheothRx Evaluation (CORE), 1996, pp. 192-201.
Zile, Michael R., et al., "New Concepts in Diastolic Dysfunction and Diastolic Heart Failure: Part II: Casual Mechanisms and Treatment", Circulation, 2002, vol. 105, pp. 1503-1508.
Canadian Patent Application No. 2,599,219 Office Action dated Jul. 16, 2009.
EP Examination Report, EP Patent Application No. 06 736 222.8 dated Jan. 27, 2010.
EP Supplemental Search Report, EP Patent Application No. 06 736 222.8 dated Sep. 29, 2008.
Examiner's Report, Australian Patent Application No. 2006216420 dated Feb. 27, 2009.
International Search Report for PCT/US2006/006862 dated Aug. 29, 2006.
International Search Report for PCT/US2007/017182 dated Dec. 17, 2008.
International Search Report for PCT/US2008/004437 dated Jan. 13, 2009.
International Search Report for PCT/US2008/013728 dated Oct. 19, 2009.
International Search Report for PCT/US2008/087185 dated Jul. 29, 2009.
Ochi, Rikuo, et al. "Electroporation of cardiac muscle: modulation by lysolipids, surfactants and polyethylene glycol", Jpn. J. Electrocardiology, vol. 20, Supp. 3, 200, pp. S-3-20-S-3-23.
Watanabe, Makino, et al., "Lysophosphatidylcholine-induced myocardial damage is inhibited by pretreatment with poloxamer 188 in isolated rat heart", Molecular and Cellular Biochemistry, vol. 248, 2003, pp. 209-215.
Ameen, V., et al., "Experimental Models of Duchenne Muscular Dystrophy: Relationship with Cardiovascular Disease", The Open Cardiovascular Medicine Journal (2010), 4:265-277 at pp. 265-277 and Fig. 2.
Beaton, L. et al., "Contraction-induced muscle damage in humans following calcium channel blocker administration", Journal of Physiology (2002), 544.3, pp. 849-859.
Brockmeier, K., et al., "X-Chromosomal (p21) Muscular Dystrophy and Left Ventricular Diastolic and Systolic Function", Pediatr Cardiol 19: 139-144, 1998.
Brooks, Susan V., "Rapid recovery following contraction-induced injury to in situ skeletal muscles in mdx mice", Journal of Muscle Research and Cell Motility 19, pp. 179-187 (1998).
Collins, J., et al., Structural and functional recovery of electropermeabilized skeletal muscle in-vivo after treatment with surfactant poloxamer 188, Biochimica et Biophysica Acta vol. 1768 (2007) 1238-1246.

(56) References Cited

OTHER PUBLICATIONS

Drexler, H., et al., "Alterations of skeletal muscle in chronic heart failure", Circulation, Journal of the American Heart Association, vol. 85, No. 5, May 1992, pp. 1715-1759.

European Search Report for EP Application No. 08861170.2 dated Mar. 11, 2011.

Horwich, T., et al., "Cardiac Troponin I is associated with impaired hemodynamics, progressive left ventricular dysfunction, and increased mortality rates in advanced heart failure", Circulation American Heart Association, (2003); 108: 833-838.

International Search Report for PCT/US2010/057560 dated Aug. 2, 2011.

Maskarinec, S., et al., "Comparative study of poloxamer insertion into lipid monolayers", Langmuir 2003, vol. 19, pp. 1809-1815.

Quinlan, John G., et al., "Poloxamer 188 failed to prevent exercise-induced membrane breakdown in mdx skeletal muscle fibers", Neuromuscular Disorders, 2006, vol. 16, pp. 856-864.

Radley, H.G., et al., "Duchenne muscular dystrophy: Focus on pharmaceutical and nutritional interventions", The INternational Journal of Biochemistry & Cell Biology, Elsevier, vol. 39, 2007, pp. 469-477.

Ryall, James G., et al., The membrane sealant poloxamer reduces membrane permeability in tibialis anterior muscles from dystrophic mdx mice, Faseb Journal, vol. 21, No. 6, Apr. 2007, pp. A945-A946, & Experimental Biology 2007 Annual Meeting; Washington, DC, USA; Apr. 28-May 2, 2007.

Scheuerbrandt, G., Approaching therapies for boys with duchenne muscular dystrophy. Parent project muscular dystrophy. Annual conference in Cincinnati/Ohio, Jul. 13-16, 2006, ACTA Myologica, Gaetano Conte Academy for the Study of Striated Muscle Diseases, Naples, IT, vol. 25, No. 2, Oct. 1, 2006, pp. 77-97.

Whitehead, Nicholas P., et al., "Streptomycin reduces stretch-induced membrane permeability in muscles from mdx mice," Neuromuscul Disord 2006, vol. 16, pp. 845-854.

Peng, Jinong et al., "Comprehensive Mutation Scanning of the Dystrophin Gene in Patients with Nonsyndromic X-Linked Dilated Cardiomyopathy", Journal of American College of Cardiology vol. 40, No. 6, pp. 1120-1124 (2002).

Mestroni Luisa, et al., "A Dilated Cardiomyopathy: Evidence for Genetic and Phenotypic Heterogeneity", Journal of American College of Cardiology vol. 34 No. 1, pp. 181-190 (1999).

* cited by examiner

LVEDP (mmHg) in Sham, heart failure animals untreated (CHF + No Rx) heart failure treated with 4.6 mg/kg P188 (CHF + 4.6) and Sham treated with 4.6 mg/kg. * P <0.05 vs CHF No rx and CHF 4.6; ** P <0.05 vs CHF No Rx and Sham ± 4.6 mg/kg. Data are mean ± SE, N = 4 for sham, 6 for CHF, 11 for (4.6 sham and CHF).

LVEF (percent) in Moderate-Severe Heart Failure animals, treated with standard and low (4.6 mcg/kg) 8 weeks after MI. Data are mean ± SE. N = 4 for sham, 6 CHF, 6 standard and 11 for 4.6. *$P < 0.05$ vs all groups. ** $P < 0.05$ vs. CHF.

LV End Diastolic Diameter (cm) in moderate-severe heart failure animals, treated with standard and low (4.6 mcg/kg) P188 8 weeks after MI.
Data are mean ± SE. N = 4 for sham, 6 for CHF and standard, 11 for low dose.
* $P < 0.05$ vs CHF and standard dose.

TREATMENT OF CHRONIC PROGRESSIVE HEART FAILURE

CROSS REFERENCE TO RELATED APPLICATION

This application is the U.S. National phase of PCT Application No. PCT/US2007/017182, filed Aug. 1, 2007, which claims the priority of U.S. Application No. 60/834,728, filed Aug. 1, 2006. Both of these documents are incorporated herein in their entirety.

BACKGROUND OF THE INVENTION

Heart failure (HF) is a syndrome or clinical condition resulting from failure of the heart to maintain adequate circulation of blood. It can be chronic or acute, and has many etiologies including ischemic infarction or myocardial infarction.

According to the American Heart Association, the total direct and indirect costs for HF in the US are estimated at $27.9 billion in 2005. The HF market has been devoid of novel drugs on the market for some time partially because drug development in the HF arena has one of the highest late stage failure rates. However, HF prevalence and incidence are increasing as a result of an aging population and increasing survival in the underlying cardiovascular disease patient base. This has resulted in an increased demand for new treatments. The US HF market is expected to grow from $1.33 billion in 2004 to $4.33 billion by 2011. Marketed products include angiotensin converting enzyme (ACE) inhibitors such as Vasotec and Altace, β-adrenergic blockers (ARBs) such as Troprol and Coreg, nitric oxide enhancing therapy (BiDil), angiotensin II receptor blockers such as Diovan and Atacand, mineralocorticoid receptor antagonists such as Inspra, and recombinant human B-type natriuretic peptide (Natrecor). There are also generic inotropes, vasodilators and diuretics. Emerging therapies include statins, inotropes with calcium sensitizer and PDE properties, recombinant erythropoietic protein, α-human natriuretic peptide, vasopressin antagonists, advanced glycation end-product (AGE) crosslink breakers, and xanthene oxidase inhibitors, among others.

In the US, there are about 5 million heart failure patients and more that 285,000 deaths occur annually from this disease (American Heart Association, Heart Disease and Stroke Statistics, 2006 Update, Dallas, Tex.). The number of patients is on the rise and is expected to reach 11.5 million in 2011 (Frost & Sullivan, U.S. Heart Failure Therapeutics Markets, F666-52, 2006; http://www.frost.com). Approximately 1.6 million patients have New York Heart Association Class III or IV HF encompassing the population with moderate to severe symptoms. These syndromes typically progress from Class III to IV over 3 to 10 years where the patients may be treated with optimal pharmacological therapy such as β-blockers, angiotensin II receptor type 1 blockers, angiotensin I converting enzyme inhibitors, calcium channel blockers, and vasodilators. As additional symptoms occur, patients may require medical devices such as implantable pacemakers or defibrillators and possibly left ventricular assist devices (LVADs). With the possible exception of LVADs, these therapies prolong life but do not stop or reverse the deterioration of heart function. In the mid- and end-stages of this disease, patients are frequently hospitalized for shortness of breath with dangerously low left ventricular ejection fraction (acute decompensation in patients with chronic HF or acute HF). These patients require IV inotropes to increase contractility of the heart muscle, IV diuretics to decrease fluid burden, and IV vasodilators to decrease peripheral vascular resistance (ACC 2005). However, patients are discharged with signs and symptoms of congestive HF and within 2 months after discharge, the readmission rate is about 30% and the mortality rate is 10%. See, e.g., Gheorghiade, M. et al., Early Management of Acute Heart Failure Syndromes, in *Cardiovascular Emergencies,* 2006, Omni, Atlanta, Mar. 11, 2006. Thus, there is an immediate and critical need for better therapies to treat acute HF.

Heart failure may be manifested by cardiac muscle dysfunction, e.g., abnormal contraction of heart muscle such as diastolic or systolic dysfunction. While several therapies are available to treat abnormal contraction, there are currently no therapies that target diastolic dysfunction of heart muscle seen in approximately 2.3 million patients. Despite various etiologies of HF, its syndromes are highly related and systolic and diastolic dysfunctions coexist in most patients. See, e.g., Dyer, G. S. M. et al., *Heart Failure,* in *Pathophysiology of Heart Disease* (L. S. Lilly ed.), Lippincott Williams & Wilkins, Baltimore, Md., 2003, p. 234. Diastolic dysfunction results from compromised ventricular heart relaxation (filling) in the presence of abnormal heart contraction and ejection fraction. See, e.g., Zile, M. R. et al., *Circulation,* 2002, 105:1387-1393. Diastolic HF DHF) is most often associated with coronary artery disease, hypertension, aging and infiltrative cardiomyopathy. Currently there are no consensus guidelines for the treatment of chronic diastolic dysfunction as compared with the ACC/AHA treatment guidelines for systolic-related HF.

Heart dysfunction may be associated with loss or lack of dystrophin in the cardiac muscle cell membrane (Takahashi, M. et al., *Eur. J. Pharmacol.,* 2005, 522: 84-93; Yasuda, S. et al., Supra; Kaprielian, R. R. et al., *Circulation,* 2000, 101: 2586-2594; Toyo-Oka, T. et al., *Proc. Natl. Acad. Sci. USA,* 2004, 101: 7381-7385). Dystrophin is a structural protein that participates in cellular organization in muscle cells and promotes both myofibril and sarcolemma (muscle cell membrane) stability. See, e.g., Kaprielian, R. R. et al., *Circulation,* 2000, 101: 2586-2594. Genetic dystrophin deficiency or abnormal dystrophin level are the underlying cause of Duchenne muscular dystrophy (MD) and Becker's muscular dystrophy (BMD), respectively. Cardiac disease in both DMD and BMD manifests as dilated cardiomyopathy (DCM), ardiac arrhythmia, or both. It is seen in young patients with an incidence of 26% by the age of 6 and causes death of these patients typically in their early to mid 20s. About 20% of DMD patients and 50% of BMD patients die from HF. Female carriers of DMD or BMD are also at risk for cardiomyopathy. For carriers the age of onset is unclear but is thought to be in the adult years. Cardiac involvement ranges from asymptomatic to severe HF. See, e.g., American Academy of Pediatrics, Clinical Report, *Pediatrics,* 2005, 116:1569-1573.

Dystrophin levels in the muscle cell membrane can also be influenced by environmental factors such as pathological stresses including catecholamine administration, coronary ligation resulting in acute myocardial ischemia, and in chronic HF after myocardial infarction (MI). The increase in intracellular calcium ($Ca^{+2}$) in HF subsequent to MI is well established with changes in calcium handling such as impaired removal of cytosolic calcium by the sarcoplasmic reticulum (SR), ryanodine receptor leakage, decreased activity of the sodium/calcium exchanger, and increased activity of phospholamban accompanying impairment of cardiac relaxation and systolic function. See, e.g., Morgan, J. P. et al., *Circulation,* 1990, 81:III21-III32; Iwanaga, Y. et al., *J. Clin Invest.,* 2004, 113:727-736; Zhang, X.-Q. et al., *J. Appl. Physiol.,* 2002, 93:1925-1931; Wehrens, X. H. et al., *Proc.*

*Natl. Acad. Sci. USA*, 2006, 103:511-518; Angeja, B. G. et al., *Circulation*, 2003, 107:659-663. These mechanisms may work to increase calcium initially leading to activation of calpains (calcium-activated proteases) and remodeling pathways. Activation of calpains could lead to initial loss of dystrophin from the membrane, causing it to become unstable and susceptible to contractile stress. The loss of dystrophin and dystrophin-associated proteins from the membranes of cardiomyocytes from HF patients and animal HF models is well documented. See, e.g., Kawada, T. et al., *Pharmacol. Therap.*, 2005, 107: 31-43; Kaprielian, R. R. et al., *Circulation*, 2000, 101:2586-2594). These proteins form complexes that provide mechanical resistance to overexpansion of the sarcolemma. Loss of these proteins is associated with an increase in the number of cardiomyocytes taking up the membrane impermeable dye Evans Blue. See, e.g., Takahashi, M. et al, *Eur. J. Pharmacol.*, 2005, 522:84-93.

Further, an increase in calpains was demonstrated in models of myocarditis where loss of dystrophin correlates with functional deficit (Lee, G.-H. et al., *Circ. Res.*, 2000, 87:489-495).

Tears in the sarcolemma have been shown to be a conduit for calcium to enter the cell and increase intracellular calcium. It has been proposed that a vicious cycle exists where stresses that cause a sustained increase in intracellular calcium, either directly or indirectly, lead to advanced HF. See, e.g., Kawada, T. et al., *Pharmacol. Therap.*, 2005, 107:31-43. In this cycle, the increased sustained calcium activates calpains which, among other things, cleave dystrophin. This leads to more membrane instability, more tears and more calcium. As the remaining cardiomyocytes are stressed because of increased work demand, they too enter this cycle.

ACE inhibitors and ARBs are drugs that have been shown to improve cardiac hemodynamics and survival in patients with heart failure. In the rat MI model of heart failure, both of these agents have been shown to prevent a decrease in the level of dystrophin from the membrane fraction of cardiac muscle cells, after MI, presumably by decreasing the total calpain content. This effect was seen when the rats were treated with these agents chronically from 2-8 weeks post infarction. See Takahashi, M. et al., *Cardiovasc. Res.* 2005, 65: 356-365.

It has also been established that sustained increases in intracellular calcium result in the activation of signaling pathways, which subsequently result in maladaptive remodeling of the heart contributing to the functional problems. See, e.g., Molkentin, J. D. et al., *Cell*, 1998, 93: 215-228; Wilkins, B. J. et al., *Circulation Research*, 2004, 94:110-8).

Taken together, it appears that dystrophin loss and membrane instability contribute to cardiac muscle dysfunction in HF.

SUMMARY OF THE INVENTION

One aspect of this invention relates to a method for treating or preventing heart failure in a subject, wherein the method includes administering to the subject in need thereof a therapeutically effective amount of a Poloxamer. As used herein, the term "therapeutically effective amount" refers to the amount of Poloxamer that can result in improvement of condition or clinical effect in a subject. As used herein, the term "subject" refers a mammal and includes, e.g., human, rat, or horse.

In some embodiments, the heart failure is ischemic heart failure.

In some embodiments the heart failure is caused by any stressor with the exception of genetic loss of dystrophin.

In some embodiments, the heart failure is chronic or acute heart failure.

In some embodiments, the Poloxamer is Poloxamer 188 (herein after "P-188") or Poloxamer 407 (hereinafter "P-407").

In some embodiments, the Poloxamer restores dystrophin levels to the cell membrane in tissue affected by HF (e.g., chronic HF). Example of the tissue and membrane includes cardiac muscle and sarcolemma, respectively.

In some embodiments, the Poloxamer is administered to the subject in need thereof over a period of 1 to 26 weeks, or over a period as long as necessarily as determined by the condition of the subject with heart failure.

In some embodiments, the Poloxamer is administered once every 1 to 15 weeks. For instance, the Poloxamer can be administered once every 1, 2, or 12 weeks.

In some embodiments, each dosage (or administration) of the Poloxamer is about 0.15 to about 480 mg/kg (e.g., about 1 to 15 mg/kg), based on the subject's weight. Specific examples of each dosage include about 1, 4.6, 10, 100, 400 mg/kg, and 460 mg/kg.

Another aspect of this invention relates to a method for improving the function of the membrane of cardiac muscle cells in a HF subject, wherein the method includes administering to the subject a therapeutically effective amount of a Poloxamer. The term "improving the function of the membrane" includes the meaning of improving the structure of the membrane and thus preventing the membrane from tearing or leaking. Examples of suitable Poloxamer include P-188 and P-407.

Another aspect of this invention relates to a method for restoring the integrity of heart muscle cell membrane in a HF subject, wherein the method includes administering to the subject a therapeutically effective amount of a Poloxamer. Examples of suitable Poloxamer include P-188 and P-407.

Still another aspect of this invention relates to a method for the treatment of skeletal muscle disease associated with dystrophy deficiency in a patient, wherein the method includes administering to the patient a therapeutically effect amount of a Poloxamer. Examples of a suitable Poloxamer include P-188 and P-407.

Yet still another aspect of this invention relates to a method for lowering and maintaining intracellular calcium levels at normal levels in a heart failure patient, wherein the method includes administering to the patient a therapeutically effective amount of a Poloxamer. Examples of suitable Poloxamer include P-188 and P-407.

Yet still another aspect of this invention relates to rapid and slow remodeling of the left ventricle within hours of administering to a patient a therapeutically effective amount of a Poloxamer. Examples of a suitable Poloxamer include P-188 and P-407.

The invention further provides a method for lowering left ventricular end-diastolic pressure (LVEDP) and increasing the left ventricular ejection fraction (LVEF) in a HF patient, comprising administering to the patient a Poloxamer. Examples of suitable Poloxamer include P-188 and P-407.

Also within the scope of this invention is the use of a Poloxamer (e.g., P-188 or P-407) for repairing the muscular tissue other than in the heart. The muscular tissue can be, e.g., of the skeletal muscle.

The invention further provides that the lowering of LVEDP can be separated from the effect of increasing LVEF by using a therapeutic amount of a Poloxamer that does not exceed 4.6 mg/kg.

In addition to the administration of a Poloxamer such as P-188 or P-407 as described above, the methods of this invention can further include additional materials in combination such as an ACE inhibitor, ARB, β-adrenergic blocker, nitric oxide enhancing therapies, mineralocorticoid receptor antagonist, recombinant human B-type natriuretic peptide, calcium channel blocker, vasodilator, diuretic, and inotropic agent.

The invention also provides a method for measuring the cell membrane sealing activities of a sealant in a subject, which includes administering the sealant into the subject, measuring and comparing the level of a leakage protein in serum before the sealant is administered to the subject and the level of the same leakage protein after the sealant is administered to the subject.

In some embodiments, the level of the leakage protein before the administration of the sealant is higher (e.g., moderately higher such as 200%, or significantly higher such as 10-fold) than the level after the administration of the same sealant.

In some embodiments, the sealant is a Poloxamer (e.g., P-188 or P-407).

In some embodiments, the subject has heart failure.

In some embodiments, the leakage protein is from the cardiamyocyte of the heart of the subject (e.g., N-terminal pro-B-type natriuretic peptide, cardiac troponin T, troponin I, or the MB isoform of creatine kinase).

Set forth below is a detailed description of this invention which is intended only for illustrative purpose and should not be interpreted as limiting the scope of this invention in any way. All publications cited herein are incorporated by reference in their entirety.

DETAILED DESCRIPTION OF THE INVENTION

Figure 1:
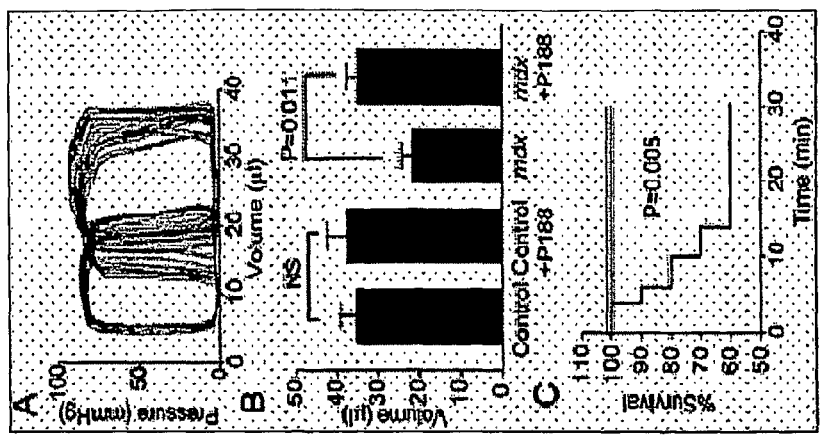
FIG. 1 shows the effect of P-188 on cardiomyocyte compliance and intracellular calcium.
Figure 1:
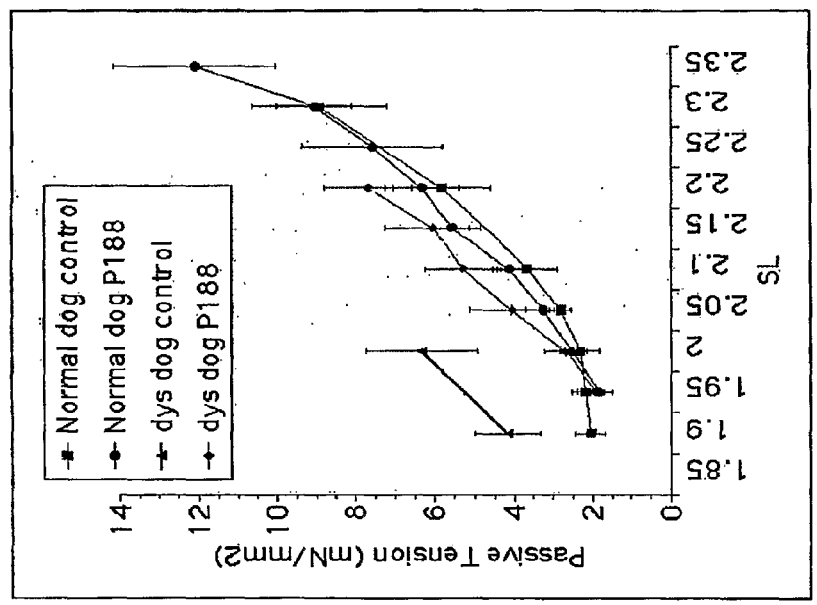
Figure 1:
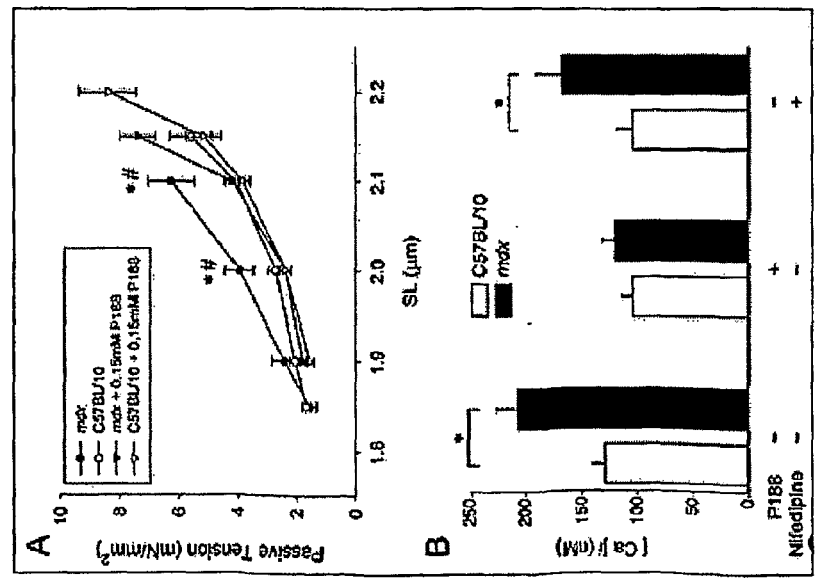

The invention provides a method for treating or preventing HF in a subject by using a therapeutically effective amount of a Poloxamer (e.g., P-188). This is based on the discovery that Poloxamers (e.g., P-188) improve cardiac hemodynamics in heart failure caused by MI which occurs because their interactions with damaged areas of membranes, where a hydrophobic area is exposed, restore cellular membrane integrity.

Poloxamers are nonionic block copolymers composed of a central hydrophobic chain of polyoxypropylene flanked by two hydrophilic chains of polyoxyethylene. Because the lengths of the polymer blocks can be customized, many different Poloxamers exist with slightly different properties. These polymers are commonly named with the word Poloxamer followed by a number to indicate which polymer is being discussed (e.g. Poloxamer 407 or Poloxamer 188).

Poloxamer 188 (P-188) is a member of the Poloxamer family. It is a nonionic triblock co-polymer of the formula poly(ethylene oxide)$_{80}$-poly(propylene oxide)$_{30}$-poly(ethylene oxide)$_{80}$ with a molecular weight of about 8,400 Dalton. This compound has several commercial names such as Pluronic F68, RheothRx, and FLOCOR. Some of its biological uses include as a stool softener in several commercially available laxatives, as an ingredient in cosmetics, and as an emulsifier for pharmaceutical agents. See, e.g., Ho, H.-O. et al., *J. Controlled Release*, 2000, 68: 433-440. P-188 has been shown to insert into lipid monolayers (Maskarinec, S. A., et al., *Biophys. J.*, 2002, 82: 1453-1459) and repair electrically damaged cell membranes (Lee, R. C., et al., *Proc. Natl. Acad. Sci. USA*, 1992, 89:4524-4528). It has also been used for controlled drug delivery, for sensitizing tumors to chemotherapy (Kabanov, A. V. et al., *Adv. Drug Delivery Rev.*, 2002, 54:759-779), and as carrier for gene therapies. P-188 has been in Phase III clinical trials for vaso-occlusive crisis in sickle cell disease (Adams-Graves, P. et al., *Blood*, 1997, 90:2041-2046; Emanuele, R. M., *Exp. Opin. Invest. Drugs*, 1998, 7:1193-1200.) and to assess thrombolytic activity in patients with acute MI (CORE) (Schaer, G. L., et al., Circulation, 1996, 94:298-307; Chareonthaitawe, P., et al., *Heart*, 2000, 84:142-148). In these trials, the efficacy of P-188 was equivocal. P-188 is safe when given acutely for up to 72 hours and well tolerated in children and adults upon repeated exposure (up to 6 exposures). See, e.g., Gibbs, W. J. et al., *Ann. Pharmacother.*, 2004, 38: 320-324. The most significant adverse effect in studies with RheothRx (P-188 of lower purity) was renal dysfunction, which however was not seen with the more pure form FLOCOR (Emanuele, R. M., supra). P-188 has a half-life of 7.5 hours in plasma of rodents and 18 hours in human subjects, but its half-life in biological membranes has not been determined. Pharmacokinetic studies have shown that less than 5% of purified P-188 is metabolized to a single metabolite of higher molecular weight and slower clearance. Renal clearance is the primary route of elimination. P-188 is non-mutagenic and does not cause chromosomal abnormalities.

Poloxamer 407 (P-407) is a hydrophilic non-ionic surfactant of the more general class of copolymers known as Poloxamers. P-407 is a triblock copolymer consisting of two hydrophilic blocks (poly-ethylene glycol) separated by a hydrophobic block (poly-propylene glycol). The approximate length of each of the two PEG blocks is 101 repeat units while the approximate length of the propylene glycol block is 56 repeat units. This particular compound is also known by the BASF trade name Lutrol F-127.

Poloxamers (including P-188 and P-407) of different grades are readily available from commercial sources, e.g., BASF. Alternatively, a skilled polymer chemist can also synthesize a Poloxamer of desired properties and molecular weight and purify it by methods known in the art. See, e.g., U.S. Pat. Nos. RE 36,665, RE 37,285, RE 38,558, 6,747,064, 6,761,824, and 6,977,045. See also Reeve, L. E., The Poloxamers; Their Chemistry and Applications, in *Handbook of Biodegradable Polymers*, Domb, A. J. et al. (eds.), Hardwood Academic Publishers, 1997. All publications cited herein are incorporated in their entireties by reference.

Poloxamers can be administering to a subject in need thereof by any appropriate route, e.g., orally or by infusion (intravenously). Assays known in the art can be used to determine the efficacy of a Poloxamer in treating heart failure, e.g., by measuring the LVEDP or LVEF.

The following examples are provided to illustrate the invention and are not intended to be limiting in any way.

Example 1

Mouse In Vitro and In Vivo Study of Membrane Integrity and Hemodynamics

Functional assays for studying active and passive force development and intracellular calcium in membrane of intact, single, adult cardiomyocytes are known in the art. See, e.g., Yasuda, S. et al., supra. This study is used to define a primary defect in cell compliance in single isolated mdx cardiomyocytes evidenced by increased susceptibility to stretch-mediated membrane instability and calcium-dependent hypercontracture.

As shown in FIG. 1, left panel, A, within the physiological range of sarcomeric length (SL) relevant to diastole (1.80-2.20 mm), P-188 fully restored mdx cardiomyocyte compliance and intracellular calcium to control levels. As shown in FIG. 1, left panel, B, Nifedipine, the L-type calcium channel blocker, did not prevent the heightened cellular calcium level in response to stretch, indicating that calcium is elevated through a different mechanism. Since calcium leak channels are not activated by stretch, calcium must enter the cell through another mechanism, e.g., through microscopic tears in the membrane. This was confirmed using a lipidic dye assay. See, e.g., Yasuda, S. et al., supra. Preliminary studies in isolated ventricular myocytes from golden retriever muscular dystrophy (GRMD) animals (see FIG. 1, Center Panel) show that the passive tension-extension curve is markedly upward and leftward shifted compared to control dog cardiomyocytes. This is evidence that the cellular compliance defect noted in cardiomyocytes from mdx mice is much more pronounced in those from GRMD dogs. In addition, it demonstrates that P-188 (150 μM) restores cellular compliance, as manifested in the shape and position of the passive tension-extension curve back nearly completely to control (see FIG. 1, right panel, part A). The magnitude of P-188's effects is therefore comparatively greater than that seen in mouse cardiac myocytes.

As shown in FIG. 1, right panel A and B, P-188 prevents cardiac dysfunction in mdx mice in vivo, which is consistent with its cellular effect of preventing stretch-induced membrane damage. Baseline left ventricular hemodynamic performance was depressed in mdx mice, including reduced left ventricular end-diastolic volume (LVEDV).

Intravenous infusion of P-188 increased LVEDV to levels seen in control hearts. Shown below in Table 1 is a summary of hemodynamic data following the infusion. The changes in hemodynamic indices provided in Table 1 suggest that the primary effect of acute P-188 administration is to restore end-diastolic volumes without significantly changing end-diastolic pressure or other parameters, consistent with P-188's effect on improving the compliance of the mdx cardiomyocytes in vitro (see FIG. 1, left panel). Cardiovascular stressors can cause acute cardiomyopathy and failure in mdx mice (Danialou, G. et al., FASEB J., 2001, 15:1655-1657). One of these stressors, an acute dobutamine stress challenge, was used to determine if P-188 could block these events in vivo. Untreated mdx mice had a very attenuated hemodynamic response to the dobutamine infusion and a significant incidence of acute cardiac failure (see FIG. 1, right panel, C) during the 30-minute stress-test regime. Pre-treatment of mdx animals with P-188 immediately improved hemodynamic response to dobutamine infusion and conferred protection from dobutamine-induced acute HF in vivo (P=0.005). These results suggest that P-188 treatment of patients in acute HF improves cardiac performance and also improves inotropic functional support.

TABLE 1

Summary of baseline hemodynamic data in mdx mice (data are mean ± SEM).

|  | C57BL/10 (n = 13) | C57BL/10 + P-188 (n = 7) | mdx (n = 13) | mdx + P-188 (n = 11) |
|---|---|---|---|---|
| Heart Rate (bpm) | 598 ± 13 | 600 ± 7 | 582 ± 10 | 585 ± 13 |
| End-Systolic Volume (mL) | 19 ± 2 | 19 ± 4 | 7 ± 1 | 13 ± 3 |
| End-Diastolic Volume (mL) | 36 ± 5 | 36 ± 4 | 22 ± 3 | 34 ± 3 |
| End-Systolic Pressure (mmHg) | 102 ± 4 | 111 ± 6 | 79 ± 3 | 76 ± 3 |
| End-Diastolic Pressure (mmHg) | 5.3 ± 0.4 | 6.1 ± 1.4 | 5.8 ± 0.5 | 7.0 ± 0.4 |
| Stroke Volume (ml) | 19 ± 2 | 19 ± 3 | 16 ± 2 | 24 ± 2 |
| $(dP/dt)_{Max}$ (mmHg/s) | 11,440 ± 660 | 13,390 ± 460 | 10,110 ± 619 | 10,880 ± 610 |
| $(dP/dt)_{Min}$ (mmHg/s) | −11,420 ± 616 | −11,810 ± 440 | −8,140 ± 580 | −7,110 ± 390 |
| Tau (msec) | 7.64 ± 0.3 | 8.4 ± 0.8 | 8.6 ± 0.5 | 9.5 ± 0.7 |

Example 2

In Vivo Study of Heart Hemodynamics in the MI Rat Heart Failure Model with High-Dose Poloxamer In the rat MI model used in this study, the left anterior descending coronary artery (LAD) was tied off to produce an infarction of greater than 40%. The rats become stable after 1-3 weeks and at Week 3 exhibited significant left ventricular dysfunction. Week-8 post-MI of these rats (HF rats) corresponded to the time of dystrophin loss. Controls include untreated HF rats, and sham-operated animals where the LAD was exposed but not tied off.

On the day of treatment, rats were infused with P-188 at 460 mg/kg over a 30-minute period and the hearts were catheterized and hemodynamics were monitored over a 4-hr period.

Compared with untreated MI rats, P-188 treatment caused a significant: 1) decrease in LVEDP, suggesting an increased ability of the heart to relax; 2) a significant (~45%) increase in LVEF, a measurement that indicates the ability of the heart to empty its content during systole; and 3) a significant decrease in isovolumic relaxation (LV−dP/dt), a measure of the rate of fall in pressure. The heart rate (HR), left ventricular systolic pressure (LVSP), left ventricular isovolumic contraction (LV+dP/dt), and left ventricular end systolic volume did not change significantly. Data from the measurements are summarized below in Table 2.

TABLE 2

Hemodynamic parameters for congestive heart failure (HF) rats untreated and treated with P-188 (460 mg/kg).

|  | HR (beats/m) | LV SP (mmHg) | LV EDP (mmHg) | LV dP/dt (+) (mmHg/sec) | LV dP/dt (−) (mmHg/sec) |
|---|---|---|---|---|---|
| HF | 245 ± 11 | 91 ± 4 | 22 ± 1 | 3574 ± 363 | 2572 ± 247 |
| HF + P-188 | 214 ± 18 | 87 ± 7 | 15 ± 2* | 3100 ± 286 | 1767 ± 249* |

Data are mean ± SE.
*$P < 0.05$ compared to HF; N = 6 in each group.

The results from this study indicate that P-188 has an effect on cardiac hemodynamics. The approximate 45% increase in LVEF is clinically significant. Ejection fraction is the percent of end-diastolic volume that is ejected as the stroke volume and is a measurement of pump function. It can be influenced by blood pressure (afterload), the amount of blood returning to the heart (preload), volume of the heart chamber, and heart rate. Our data indicate that P-188 treatment did not affect HR, and did not increase afterload because LVSP did not rise. Thus it appears that P-188 has an effect on preload, which can be influenced by venous return of blood to the heart as well as compliance of heart muscle. LVEDP, also influenced by these parameters, is decreased in our experiments. Since a significant drop in venous return should be accompanied by a change in blood pressure, which is not seen with P-188. The results suggest that P-188 increases the compliance of the working heart.

Example 3

In Vivo Study of Heart Hemodynamics in the MI Rat Heart Failure Model with Low Dose Poloxamer On the day of treatment, rats were infused with P-188 at 4.6 mg/kg over a 30-minute period and the hearts were catheterized and hemodynamics monitored over a 4-hr period. Some animals were monitored by echocardiography.

Figure 2:
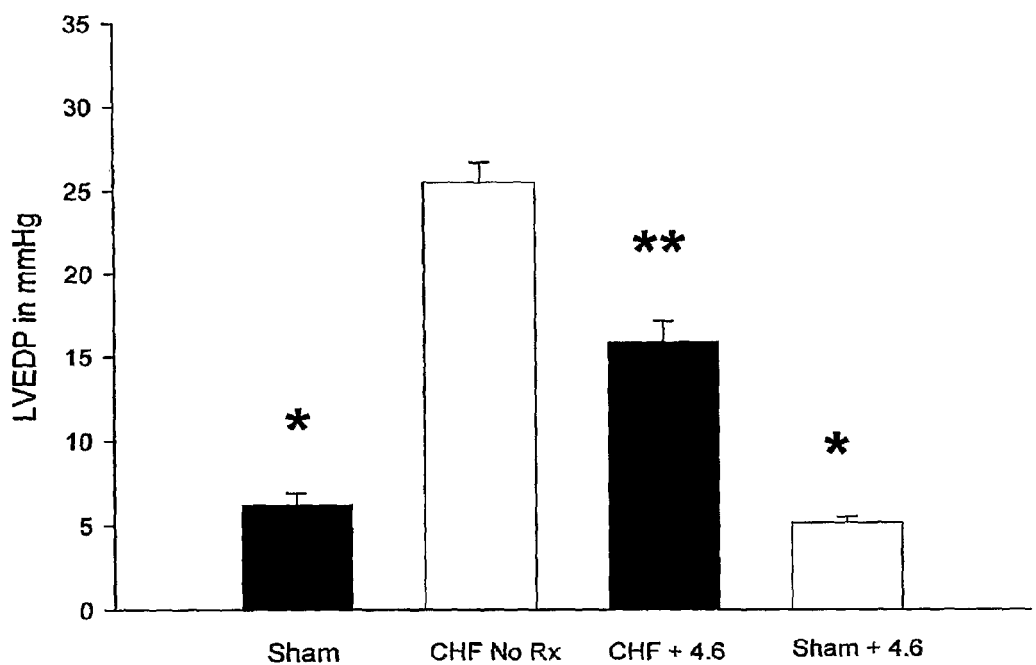
FIG. 2 shows the effect of P-188 on left ventricular end diastolic pressure.

As shown in FIG. 2, congestive heart failure (CHF) and sham-operated control rats were treated or not with 4.6 mg/kg P-188 over a 30-minute interval and LVEDP was measured at 4 hr post dosing. Untreated CHF rats exhibited a 20 mm pressure rise in LVEDP developed over the 8-week interval between infarction and treatment. Treatment with 4.6 mg/kg of P-188 decreased LVEDP by 9 mm Hg compared to untreated CHF animals. P-188 treatment at this dose had no effect on LVEDP in sham-operated control rats.

Figure 3:
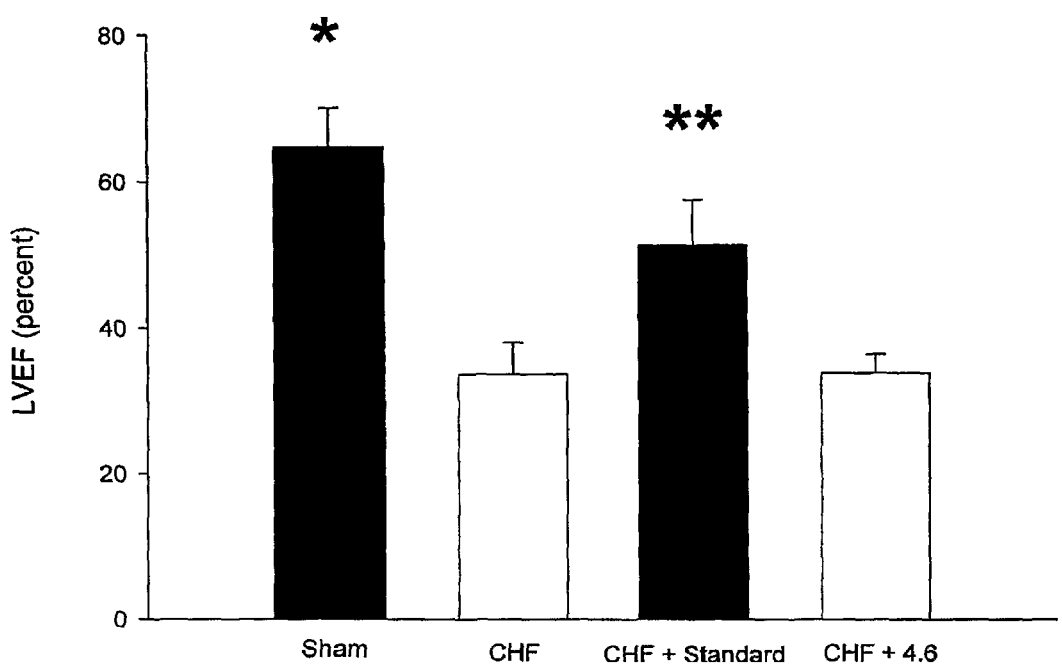
FIG. 3 shows the effect of P-188 on left ventricular ejection fraction.

As discussed above, P-188 treatment of CHF rats caused an increase in LVEF at the 460 mg/kg dose. At 4.6 mg/kg, P-188 had no effect on LVEF compared with untreated CHF rats (see FIG. 3). This result was surprising and completely unexpected since the effect on LVEDP was maintained or even enhanced at the 4.6 mg/kg dose.

The results from the high and low dose experiments indicate that the effect of P-188 on lowering of LVEDP can be separated from the effect on LVEF. These results suggest the possibility that significantly greater membrane repair is required for the effect on LVEF. Thus, P-188 treatment over a 4.6 to 460 mg/kg dose range caused a drop in LVEDP in CHF rats that is statistically and potentially clinically significant. The results suggest that P-188 at doses lower than 4.6 mg/kg may be effective in decreasing LVEDP.

Figure 4:
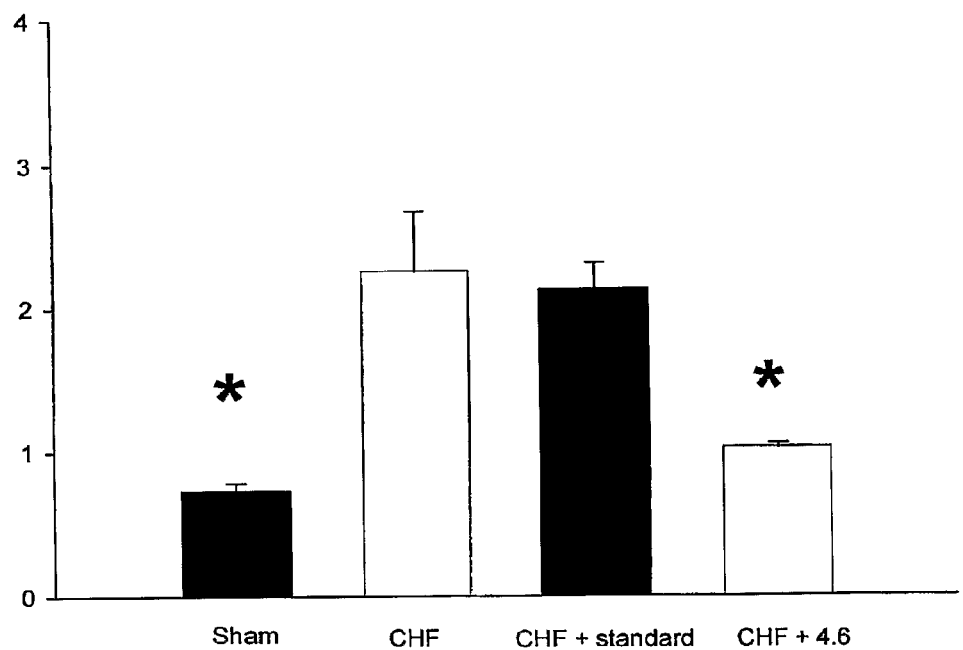
FIG. 4 shows the effect of P-188 on left ventricular end-diastolic diameter.

In addition to the drop of LVEDP in CHF rats treated with 4.6 mg/kg of P-188, a decrease in left ventricular end-diastolic diameter (LVEDD) was also observed (see FIG. 4). This decrease represents a movement toward normal LVEDD. This was surprising in light of the fact that this measurement was taken at 4 hr post-treatment. This rapid remodeling of the heart muscle was unexpected and such a rapid remodeling has not been previously reported for any heart failure treatment.

No significant change in LVEDD was observed at the high dose by echocardiography. The reason for this remains to be established but it is possible that non-specific effects at the high dose of P-188 might mask the mechanistic effects of this class of compounds.

The separation of P-188 effects based on dosage is clinically useful. In chronic heart failure patients that have acute decompensation episodes, LVEF can fall to a dangerously low level. In such patients, a dose of P-188 greater than 4.6 mg/kg could be used to increase ejection fraction to help reestablish a compensated state. In stable patients with chronic heart failure (sufficiently high ejection fraction) a dose of P-188 at or below 4.6 mg/kg would be useful in maintaining left ventricular compliance and in maintaining the diameter of this chamber of the heart.

Example 4

Chronic Treatment of Heart Failure in the Rat MI Model of Heart Failure with P-188

The study occurs over an 18-week period. Table 3 below illustrates the design and flow of the possible study. Specifically, rats are acclimated to 12 hours day night cycles for 2 weeks prior to the study. Groups are labeled by the number of weeks post MI (W) that the animals are used. Treatment with P-188 is indicated as T and NT stands for non-treatment. The number of rats in each group at the beginning of the study is scaled to account for a 25% mortality at 1 week post MI. Hemodynamic measurements (Hemo-meas.) are made on each 16W group (N=12). All hearts from remaining animals are harvested and flushed with ice-cold buffer and used in experiments outlined in other examples described below. Blood samples are collected from all rats in EDTA collection tubes and used later. Myocardial infarction is induced by ligation of the left anterior descending coronary artery (LAD) as described in Day, S. M. et al., Supra; Tarnavski, O. et al., *Physiol. Genomics,* 2004, 16: 349-360; with modifications for the model. Briefly, Sprague-Dawley rats (250-300 g) are anesthetized with intraperitoneal ketamine (50 mg/kg) and xylazine (5 mg/kg), intubated and mechanically ventilated with 2% isoflurane. A left thoracotomy is performed and the proximal LAD is encircled with a suture. The suture is ligated and occlusion confirmed by the change in color (to pale) of the anterior wall of the LV. Sham-operated controls will not have the suture ligated. For the MI rats, a mortality rate of approximately 25%/o is expected in the first week. Fifty-six rats representing those that receive P-188 treatment or vehicle are anesthetized as described above on week 9 post MI. A urethane coated antithrombogenic vascular catheter is inserted into the jugular vein and exteriorized at the dorsal side of the neck. The catheter is filled with saline and heparin and closed (see, e.g., http://www.braintreesci.com/Thoracic.htm). Starting with the 13$^{th}$ week post-MI, these 28 rats are infused daily, weekly, every other week, or monthly with P-188, with a dosage of between 1 and 480 mg/kg (e.g., at about 4.6 mg/kg or 460 mg/kg) at a rate of 0.2 mL/Kg/minute.

TABLE 3

| Design for In Life Procedure | | | | | | | | | | | |
|---|---|---|---|---|---|---|---|---|---|---|---|
| Group | 16W NT | 16W T | 16W NT | 12W NT | 8W NT | 4W NT | 4W NT | 8W NT | 12W NT | 16W T | 16W NT |
| Group | | | | | | | | | 16W NT | | |
| Week | 1 | 2 | 3 | 4 | 5 | 6 | 10 | 13 | 16 | 17 | 18 |

TABLE 3-continued

Design for In Life Procedure

| # Rats | 32 | 32 | 32 | 19 | 19 | 19 | | | | | |
|---|---|---|---|---|---|---|---|---|---|---|---|
| # Rats sac. | | | | | | | 14 | 14 | 42 | 28 | 28 |
| Procedure | MI | MI | Sham | MI | MI | MI | | | | | |
| # rats/day | 8 | 8 | 8 | 8/3 | 8/3 | 8/3 | | | | | |
| # days/wk | 4 | 4 | 4 | 2/1 | 2/1 | 2/1 | | | | | |
| Hemo meas. | | | | | | | — | — | 16W NT (12) | 12 | 12 |
| Hearts other | | | | | | | 14 | 14 | 30 | 16 | 16 |
| Serum | | | | | | | 14 | 14 | 42 | 28 | 28 |

When more than two data sets are compared, analysis of variance (ANOVA) is used to examine whether significant differences exist between groups. When interactions among the various groups are indicated by ANOVA, a Student's-Neuman-Keuls post hoc test is used to determine significant differences between two mean values. The mean value is derived from a sample size of at least 5 observations. Probability is set at lower than 0.05.

Example 5

Determination of Effect on Dystrophin Levels in Chronic Heart Failure Rats

It has been shown that dystrophin deficiency has a profound effect to slow relaxation performance in single myocytes under physiological load. P-188 acutely corrected this relaxation defect. See, e.g., Yasuda, S. et al., supra.

Loss of dystrophin from the sarcolemma of cardiomyocytes from the MI rat is followed out to 8 weeks post MI. It is important to know whether or not this loss is progressive since the magnitude of the response to P-188 may be directly related to membrane fragility and the number of microscopic tears. This information might be useful in predicting patient outcomes based on the history of their disease.

In this study, dystrophin and other membrane proteins are evaluated by both western blotting and by immunohistochemistry according to procedures described in Dai et al., *J. Biol. Chem.*, 2002, 276: 37178-37185; Molkentin et al., *J. Biol. Chem.*, 1993, 268: 19512-19520. Western blotting is used to measure dystrophin in the membrane fraction from cells in the non-infracted area of the heart. A minimum of 6 MI hearts are analyzed from each time point and are taken from animals after hemodynamic parameters have been determined (see below). The sarcolemma fraction is prepared and the cytosolic fraction is frozen and stored at −80° C. After protein determination, an equal amount of protein from each sample is run on a 6% or 12% SDS-polyacrylamide gels and blotted to polyvinylidene fluoride (PVDF) membrane and the appropriate proteins detected with their respective antibodies. The antibodies to be used are against dystrophin, α-sarcoglycan (α-SG), β-sarcoglycan, γ-sarcoglycan (γ-SG) and β-dystroglycan, which are commercially available (e.g., from Novocastra). It has been shown previously that while dystrophin and α-SG decrease at 8-weeks post MI, γ-SG remains unchanged. See, e.g., Yoshida, H. et al., *Cardiovas. Res.*, 2003, 59: 419-427). As such γ-SG is used as a loading control. Levels of these proteins in the MI rats are compared with those in both un-operated and sham operated control hearts to determine the relative decrease in dystrophin and α-SG over time.

Non-infracted LV and septum of MI and control hearts are homogenized in 5 volumes of ice-cold buffer (300 mM phenylmethylsulfonyl fluoride (PMSF), 320 mM sucrose, 1 mM EGTA, 20 mM Tris-HCL pH 7.4). The homogenate is centrifuged at 1000×g at 4° C. for 10 min. The supernatant fluid is centrifuged at 8000×g for 20 minutes and the resultant supernatant fluid is re-centrifuged at 100,000×g for 20 minutes at 4° C. The resultant pellet, the sarcolemma fraction, is resuspended in buffer without PMSF and protein concentration determined (Yoshida, H. Supra). The supernatant fluid is the cytosolic fraction. This fraction is concentrated, separated by electrophoresis and blotted for cleavage products or membrane-dissociated proteins if data from the membrane fraction is not definitive.

Immunohistochemistry is conducted to determine if any change in membrane dystrophin reflects large loss in a few myocytes or a more general effect. Hearts are frozen in isopentane chilled in liquid nitrogen. 4-10 μm sections are cut and air-dried on slides coated with section adhesive. The unfixed section is incubated with primary antibody for 1 hr at 25° C., washed 3 times each for 10 minutes in buffer (1% bovine serum albumin/phosphate buffered saline (PBS)), and then incubated with fluorescently labeled secondary antibody for 1 hour at 25° C. The section is then washed three times with buffer. Sections are then mounted in Vectashield (Vector Labs) and visualized by confocal microscopy. Digital photographs are taken of each section. To confirm membrane localization of dystrophin, some serial sections are incubated with antibodies against vinculin and compared with dystrophin staining.

After blotting and antibody staining, proteins on the western blots are visualized by enhanced chemiluminescence and the bands developed on X-ray film. The bands on the film are quantitated by densitometry and normalized to γ-SG in order to compare between gels. Loading is also checked by Coomasie Blue staining of the gels. For western blots, equal amounts of protein/lane. Images of cryosections are analyzed using Image Pro image analysis software. However, the latter are intended to be used to determine the breadth of the dystrophin/a-SG loss across the non-infracted regions of the heart.

If no further diminution in these protein levels is observed at later times it may be that the changes are too small to be detected. An inability to see a significant change past 8 weeks post MI indicates that the significant change to membrane stability occurs early and that P-188 effectively reduces the dystrophy levels (by 25-30%) and also reduces the α-SG level by 40-50%) after 8-weeks from the MI.

Example 6

Identification of Membrane Leakage

At 8 weeks post MI, a loss of integrity in the sarcolemma cardiac myocytes has been demonstrated by showing uptake of the membrane impermeable dye Evans Blue (EB) in isolated cells Kawada T., supra. (EB dye forms a tight complex with albumin and it is this complex that is taken up by damaged cells). The EB method for assessing cardiac and skeletal muscle damage is used as described in Straub, V. et al., *J. Cell Biol.*, 1997, 139: 375-385; Bansal, V. et al., *Nature*, 2003, 423:168-172; Coral-Vazquez, R. et al., *Cell*, 1999, 20: 465-474.

Rats for this study are accounted for as in Table 2. At each time point, animals N=6-7) are removed from the study and injected with a sterile EB dye solution in their tail vein. EB dye is dissolved in PBS (10 mg/ml) and sterilized by passage through membrane filters with a pore size of 0.2 mm. Rats are injected with 0.025 mL/g of body weight of the dye solution, and sacrificed 6 hours after EB dye administration. During the time between injection and sacrifice, the rats will be housed in standard laboratory cages. Cardiac muscle sections for microscopic EB detection will be incubated in ice-cold acetone at −20° C. for 10 minutes, rinsed with PBS and mounted with Vectashield mounting medium (Vector Labs). The heart sections will be viewed by fluorescence microscopy where EB stained regions appear red. All sections are photographed and photos analyzed to determine the areas of the EB positive and negative cell staining. These areas are compared to those in sham-operated animals (N=7) as well as those from an un-operated cohort (N=12).

From each heart, 5-7 of 7-mm sections is mounted and photographed. Photographs are analyzed using Image Pro software. Areas stained with EB dye are traced and the area within the trace quantitated. This is normalized to the area of the non-infracted tissue in the section. Similar sections are taken from hearts at different times. In this way, it is determined whether the number of EB staining cells is increasing post MI. When more than two data sets are compared, analysis of variance (ANOVA) is used to examine whether significant differences exist between groups. When interactions among the various groups are indicated by ANOVA a Student's-Neuman-Keuls post hoc test is used to determine significant differences between two mean values. The mean value is derived from a sample size of at least 5 observations. Probability is set at less than 0.05.

It is expected that Evans Blue staining areas will not be seen in the hearts from sham-operated controls or from normal Sprague-Dawley rats. At 12 and 16-weeks post MI an increase in the number of compromised cells is anticipated although this may not be as large an increase as seen between 4 and 8 weeks. This may be due to the prolonged stable phase of heart failure seen in this model.

Example 7

Effect of Chronic Treatment on Cardiac Hemodynamics

As outlined above in Table 3, rats are catheterized and treated with purified P-188 for 4 weeks total (16WT group) or vehicle (16W NT) from 12-16 weeks post MI. The 16WNTS group are not catheterized or do not receive vehicle. At 16 weeks post MI, these animals are anesthetized, intubated and mechanically ventilated. A median sternotomy is performed and a pressure-volume conductance catheter inserted into the LV through the apex to obtain hemodynamic data, which is analyzed with ARIA 1 Pressure-Volume Analysis software (Milar Instruments). The following parameters are analyzed: maximum LV ejection fraction, stroke volume, −dP/dT, end-systolic volume, end-systolic pressure, end diastolic pressure, end diastolic volume, and −dP/dT. After measurements, the animals will be terminated and blood will be collected for serum and hearts will be frozen as described in specific aim 2 for immunohistochemistry.

Based on the hypothesis that P-188 works by repairing these compromised areas, it might be expected that P-188 would have a larger effect in hearts where, prior to cell death, more cells are compromised. It is also expected that if more cells are compromised, more dystrophin will be lost from the membrane. Here we will determine if the number of compromised cardiac myocytes increases at over the 16-week in life portion of the study.

We expect that P-188, in the chronic dosing paradigm, will improve LVEDP and thereby diastolic dysfunction at 16 weeks post MI. These results will be compared to the 8-week post MI model (acute dosing) to begin to study the potential affect of remodeling on P-188 efficacy. At high doses (e.g. 460 mg/kg) P-188 treatment is also expected to improve systolic function by increasing LVEF. Regardless of the outcome of this study, the results obtained will provide significant insight into the efficacy of P-188, the type of patient who should be treated, and the clinical outcomes expected. These results will be invaluable to the design of potential clinical trials.

Example 8

Determine in the Rat if Serum Markers of Myocardial Damage are Increased During HF, and if P-188 Treatment Lowers the Levels of These Markers There are several reports in the literature that indicate that the serum levels of some cardiac proteins (leakage proteins) are elevated with no evidence of an acute ischemic event or sites of detectable necrosis (Tschope, C. et al., *J. Card. Fail.*, 2005, 11: Suppl. S28-S33; Nunes, J. P., *Rev. Port. Cardiol.*, 2001, 20: 785-788; Zhu, T. et al., *Circulation*, 2005, 112: 2650-2659; Lowbeer, C. et al., *Scand. J. Clin. Lab Invest.*, 2004, 64: 667-676. In Zhu, T. et al., supra, it is suggested that membrane integrity is restored by the replacement of δ-SG and subsequently CK-MB levels in serum decrease. In Nunes, J. P., supra, it is suggested that TnI might be released from myocardial cells without complete disruption of the membrane. These papers suggest that markers, typically associated with necrotic damage, can be leaked. It is believed that these makers are leaked through tears in the myocyte sarcolemma that may be repairable. Therefore, an increase in the levels of these markers in serum, from 4 to 16 weeks post MI may be a measure of membrane tears that are, in part, repairable. If P-188 works by repairing these tears, then a decrease in the serum level of these markers would be expected and could be used as potential clinical mechanism biomarkers for P-188 therapy.

Serum levels of cardiac muscle damage markers cardiac troponin I (cTnI), cardiac troponin T (cTnT), creatine kinase brain and muscle isoforms (CK-MB and CK-M and CK-B), pro brain natriuretic peptide (proBNP), atrial natriuretic peptide (ANP), myosin light chain I (MLC-I), and heart fatty acid binding protein (hFABP) are measured along with dystrophin and potentially leptin (Schulze, P. C. et al., *Clin. Chem. Acta*, 2005, 362:1-11). Rat cTnI, and hFABP ELISA kits are available from Life Diagnostic, rat BNP from BioCat, rat ANF from Blossom Biotechnologies and rat leptin from several commercial sources. Antibody pairs for development of ELISAs of rat CK-MB, cTnT, MLC-1 and dystrophin are commercially available. The development of ELISAs has been standardized and put into kit form by several manufacturers.

They are all similar in content but differ in detection methods and in procedure depending on the type of antibodies used. The respective antigens for these antibodies are also commercially available and can be used for determining the sensitivity and linearity of the assays. Prior to assaying serum from each of the MI rats, serum from a minimum of 20 control Sprague-Dawley rats are assayed for each protein to set a baseline ranges. Two normal rats receive EB dye infection 6 hr prior to sacrifice to determine the effect of this agent on the ranges of cardiac markers. Blood is collected in a centrifuge tube from each rat, shown in the in life portion of the experiment, at sacrifice, the red blood cells are allowed to clot for 15 minutes at the room temperature and centrifuged at 1500 RPM in a table top centrifuge. The serum is frozen and stored at −80° C. until use.

Serum are collected from each animal, including those treated with EB dye to determine any consistent differences between marker levels from EB dye treated and untreated animals. The amount of marker present in the serum sample of each animal is quantitatively determined using a standard curve and will be expressed as mg/ml. For CK, the amount of the cardiac MB is determined, as well as CK-M and B, so that it can be expressed as the ratio of $CK\text{-}MB/CK_{total}$ to accurately reflect that derived from compromised cardiac myocytes.

Given the foregoing, it is expected that one or more of the selected markers will show a sustained increase from 8-16 weeks post MI and P-188 treatment for 4 weeks is expected to cause a decrease, closer to the normal range, in the level of all markers that are elevated. This result would suggest that P-188 stimulates the cardiomyocyte to repair its sarcolemma and would provide evidence that this biomarker that could be used in clinical trials.

What is claimed is:

1. A method of treating systolic dysfunction in a systolic heart failure subject by decreasing left ventricular end-diastolic pressure (LVEDP) and increasing left ventricular ejection fraction (LVEF) without significantly increasing left ventricular end systolic volume, comprising administering to the subject in need thereof a therapeutically effective amount of a Poloxamer-188 ranging from greater than 4.6 mg/kg to 460 mg/kg.

2. The method of claim 1, wherein administration of Poloxamer-188 restores dystrophin levels in the heart.

3. The method of claim 1, wherein the Poloxamer is administered over a period of 1 to 26 weeks.

4. The method of claim 1, wherein the subject's systolic heart failure arises after an acute myocardial infarction.

* * * * *